US008449452B2

(12) United States Patent
Iddan et al.

(10) Patent No.: US 8,449,452 B2
(45) Date of Patent: May 28, 2013

(54) IN-VIVO SENSING SYSTEM

(75) Inventors: Gavriel J. Iddan, Haifa (IL); Zvika Gilad, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 2042 days.

(21) Appl. No.: 10/529,735

(22) PCT Filed: Sep. 30, 2003

(86) PCT No.: PCT/IL03/00784
§ 371 (c)(1),
(2), (4) Date: Mar. 30, 2005

(87) PCT Pub. No.: WO2004/028335
PCT Pub. Date: Apr. 8, 2004

(65) Prior Publication Data
US 2006/0004255 A1    Jan. 5, 2006

Related U.S. Application Data

(60) Provisional application No. 60/414,339, filed on Sep. 30, 2002, provisional application No. 60/458,441, filed on Mar. 31, 2003.

(51) Int. Cl.
*A61B 1/04* (2006.01)
(52) U.S. Cl.
USPC ............................... 600/109; 600/160
(58) Field of Classification Search
USPC ......... 600/549, 101, 104, 106, 109, 114–117, 600/143, 151, 160
See application file for complete search history.

(56) References Cited

U.S. PATENT DOCUMENTS

| | | |
|---|---|---|
| 3,683,890 A | 8/1972 | Beal |
| 3,971,362 A | 7/1976 | Pope et al. |
| 4,109,644 A | 8/1978 | Kojima |
| 4,172,446 A * | 10/1979 | Bucalo .................... 600/582 |
| 4,178,735 A | 12/1979 | Jackson |
| 4,239,040 A | 12/1980 | Hosoya et al. |
| 4,262,632 A | 4/1981 | Hanton et al. |
| 4,278,077 A | 7/1981 | Mizumoto |

(Continued)

FOREIGN PATENT DOCUMENTS
DE    2929429    2/1980
DE    34 40 177    6/1986
(Continued)

OTHER PUBLICATIONS

U.S. Appl. No. 09/807,892, filed Jun 6, 2001, Meron et al.

(Continued)

*Primary Examiner* — Rene Towa
(74) *Attorney, Agent, or Firm* — Pearl Cohen Zedek Latzer, LLP

(57) ABSTRACT

An in-vivo sensing system incorporating a sensing device movably disposed within a housing such that the orientation of the sensing device may be moved or changed in response to substantially small forces. The in-vivo sensing device may be ingested and may naturally traverse a lumen such as the GI tract or may be anchored at a surgical site. In a preferred embodiment, the in vivo sensing system is an imaging system (100) incorporating a sensing device such as an imaging device (112) suspended in a liquid (114) encapsulated in an covering or housing (110).

5 Claims, 6 Drawing Sheets

U.S. PATENT DOCUMENTS

| | | | |
|---|---|---|---|
| 4,439,197 A | 3/1984 | Honda et al. | |
| 4,481,952 A | 11/1984 | Pawelec | |
| 4,646,724 A | 3/1987 | Sato et al. | |
| 4,689,621 A | 8/1987 | Kleinberg | |
| 4,803,992 A | 2/1989 | Lemelson | |
| 4,819,620 A | 4/1989 | Okutsu | |
| 4,844,076 A | 7/1989 | Lesho et al. | |
| 4,901,143 A | 2/1990 | Uehara et al. | |
| 4,936,823 A | 6/1990 | Colvin et al. | |
| 4,940,997 A | 7/1990 | Hamlin et al. | |
| 5,010,412 A | 4/1991 | Garriss | |
| 5,042,486 A | 8/1991 | Pfeiler et al. | |
| 5,081,041 A | 1/1992 | Yafuso et al. | |
| 5,109,870 A | 5/1992 | Silny et al. | |
| 5,187,572 A | 2/1993 | Nakamura et al. | |
| 5,211,165 A | 5/1993 | Dumoulin et al. | |
| 5,241,170 A | 8/1993 | Field, Jr. et al. | |
| 5,267,033 A | 11/1993 | Hoshino | |
| 5,279,607 A | 1/1994 | Schentag et al. | |
| 5,318,557 A * | 6/1994 | Gross | 604/891.1 |
| 5,330,427 A | 7/1994 | Weissenburger | |
| 5,337,732 A | 8/1994 | Grundfest et al. | |
| 5,368,027 A | 11/1994 | Lubbers et al. | |
| 5,395,366 A | 3/1995 | D'Andrea et al. | |
| 5,398,670 A | 3/1995 | Ortiz et al. | |
| 5,420,631 A | 5/1995 | Hamasaki | |
| 5,429,132 A | 7/1995 | Guy et al. | |
| 5,479,935 A | 1/1996 | Essen-Moller | |
| 5,495,114 A | 2/1996 | Adair | |
| 5,547,455 A * | 8/1996 | McKenna et al. | 600/113 |
| 5,549,109 A | 8/1996 | Samson et al. | |
| 5,558,640 A | 9/1996 | Pfeiler et al. | |
| 5,604,531 A | 2/1997 | Iddan et al. | |
| 5,697,384 A | 12/1997 | Miyawaki et al. | |
| 5,734,418 A | 3/1998 | Danna | |
| 5,754,313 A | 5/1998 | Pelchy et al. | |
| 5,800,350 A | 9/1998 | Coppelson et al. | |
| 5,812,187 A | 9/1998 | Watanabe | |
| 5,819,736 A | 10/1998 | Avny et al. | |
| 5,833,603 A * | 11/1998 | Kovacs et al. | 600/317 |
| 5,837,196 A | 11/1998 | Pinkel et al. | |
| 5,908,294 A | 6/1999 | Schick et al. | |
| 5,913,820 A | 6/1999 | Bladen et al. | |
| 5,929,901 A | 7/1999 | Adair et al. | |
| 5,986,693 A | 11/1999 | Adair et al. | |
| 5,993,378 A | 11/1999 | Lemelson | |
| 6,043,839 A | 3/2000 | Adair et al. | |
| 6,088,606 A | 7/2000 | Ignotz et al. | |
| 6,099,482 A | 8/2000 | Brune et al. | |
| 6,145,393 A * | 11/2000 | Canton | 74/5.43 |
| 6,149,581 A | 11/2000 | Klingenstein | |
| 6,174,291 B1 | 1/2001 | McMahon | |
| 6,228,048 B1 | 5/2001 | Robbins | |
| 6,233,476 B1 | 5/2001 | Stormmer et al. | |
| 6,240,312 B1 | 5/2001 | Alfano et al. | |
| 6,276,605 B1 | 8/2001 | Olmstead et al. | |
| 6,285,897 B1 * | 9/2001 | Kilcoyne et al. | 600/350 |
| 6,324,418 B1 | 11/2001 | Crowley et al. | |
| 6,369,812 B1 | 4/2002 | Lyriboz et al. | |
| 6,395,562 B1 | 5/2002 | Hammock et al. | |
| 6,449,006 B1 | 9/2002 | Shipp | |
| 6,453,199 B1 | 9/2002 | Kobozev | |
| 6,475,145 B1 | 11/2002 | Baylor | |
| 6,488,694 B1 | 12/2002 | Lau et al. | |
| 6,570,617 B2 | 5/2003 | Fossum et al. | |
| 6,626,834 B2 * | 9/2003 | Dunne et al. | 600/444 |
| 6,632,175 B1 | 10/2003 | Marshall | |
| 6,692,430 B2 | 2/2004 | Adler | |
| 6,803,947 B1 | 10/2004 | Tomioka | |
| 6,929,636 B1 * | 8/2005 | von Alten | 604/890.1 |
| 2001/0017649 A1 | 8/2001 | Yaron | |
| 2001/0025135 A1 | 9/2001 | Naito et al. | |
| 2001/0035902 A1 | 11/2001 | Iddan et al. | |
| 2001/0051766 A1 | 12/2001 | Gazdzinski | |
| 2001/0052930 A1 | 12/2001 | Adair et al. | |
| 2002/0015952 A1 | 2/2002 | Anderson et al. | |
| 2002/0057294 A1 | 5/2002 | Ejima et al. | |
| 2002/0103417 A1 | 8/2002 | Gazdzinski | |
| 2002/0109774 A1 * | 8/2002 | Meron et al. | 348/74 |
| 2002/0134911 A1 | 9/2002 | Zarnowski et al. | |
| 2002/0146368 A1 | 10/2002 | Meron et al. | |
| 2002/0158976 A1 | 10/2002 | Vni et al. | |
| 2002/0161282 A1 | 10/2002 | Fulghum | |
| 2002/0171669 A1 | 11/2002 | Meron et al. | |
| 2002/0173718 A1 | 11/2002 | Frisch et al. | |
| 2002/0177779 A1 | 11/2002 | Adler et al. | |
| 2002/0193664 A1 | 12/2002 | Ross et al. | |
| 2002/0198439 A1 | 12/2002 | Mizuno | |
| 2003/0004562 A1 * | 1/2003 | DiCarlo | 623/1.13 |
| 2003/0018280 A1 | 1/2003 | Lewkowicz et al. | |
| 2003/0020810 A1 | 1/2003 | Takizawa et al. | |
| 2003/0023150 A1 | 1/2003 | Yokoi et al. | |
| 2003/0028078 A1 | 2/2003 | Glukhovsky | |
| 2003/0043263 A1 | 3/2003 | Glukhovsky et al. | |
| 2003/0045790 A1 | 3/2003 | Lewkowicz et al. | |
| 2003/0077223 A1 | 4/2003 | Glukhovsky et al. | |
| 2003/0114742 A1 | 6/2003 | Lewkowicz et al. | |
| 2003/0117491 A1 | 6/2003 | Avni et al. | |
| 2003/0130562 A1 * | 7/2003 | Barbato et al. | 600/109 |
| 2003/0151661 A1 | 8/2003 | Davidson et al. | |
| 2003/0167000 A1 * | 9/2003 | Mullick et al. | 600/424 |
| 2003/0171648 A1 | 9/2003 | Yokoi et al. | |
| 2003/0171649 A1 | 9/2003 | Yokoi et al. | |
| 2003/0171652 A1 | 9/2003 | Yokoi et al. | |
| 2003/0195415 A1 | 10/2003 | Iddan | |
| 2003/0208107 A1 | 11/2003 | Refael | |
| 2003/0214579 A1 | 11/2003 | Iddan | |
| 2003/0214580 A1 | 11/2003 | Iddan | |
| 2003/0216622 A1 | 11/2003 | Meron et al. | |
| 2004/0027459 A1 | 2/2004 | Segawa et al. | |
| 2004/0027500 A1 | 2/2004 | Davidson et al. | |
| 2004/0258328 A1 | 12/2004 | Adler | |
| 2005/0119577 A1 * | 6/2005 | Taniguchi | 600/459 |

FOREIGN PATENT DOCUMENTS

| | | |
|---|---|---|
| EP | 0667115 | 4/1995 |
| FR | 2 688 997 | 10/1993 |
| FR | 02237648 | 2/1995 |
| IL | 126727 | 10/1998 |
| IL | 143258 | 5/2001 |
| IL | 143259 | 5/2001 |
| JP | 4109927 | 4/1992 |
| JP | 4144533 | 5/1992 |
| JP | 5015515 | 1/1993 |
| JP | 6114037 | 4/1994 |
| JP | 6285044 | 10/1994 |
| JP | 7111985 | 5/1995 |
| JP | 7289504 | 11/1995 |
| JP | 2000342522 | 12/2000 |
| JP | 2001091860 | 4/2001 |
| JP | 2001095755 | 4/2001 |
| JP | 2001095756 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001112709 | 4/2001 |
| JP | 2001112710 | 4/2001 |
| JP | 2001112740 | 4/2001 |
| JP | 2001137182 | 5/2001 |
| JP | 2001224551 | 8/2001 |
| JP | 2001224553 | 8/2001 |
| JP | 2001231744 | 8/2001 |
| JP | 2001245844 | 9/2001 |
| JP | 2002010990 | 1/2002 |
| JP | 2000342524 | 6/2002 |
| JP | 2000342525 | 6/2002 |
| WO | WO 98-11816 | 3/1998 |
| WO | WO 99/32028 | 7/1999 |
| WO | WO 01-08548 | 2/2001 |
| WO | WO 01-10291 | 2/2001 |
| WO | WO 01/50941 | 7/2001 |
| WO | WO 01-65995 | 9/2001 |
| WO | WO 01/69212 | 9/2001 |
| WO | WO 2004/088448 | 10/2001 |
| WO | WO 02-054932 | 7/2002 |

| | | |
|---|---|---|
| WO | WO 02/055126 | 7/2002 |
| WO | WO 02/055984 | 7/2002 |
| WO | WO 02-067593 | 8/2002 |
| WO | WO 02-080376 | 10/2002 |
| WO | WO 02/094337 | 11/2002 |
| WO | WO 03/003706 | 1/2003 |
| WO | WO 03/011103 | 2/2003 |
| WO | WO 2004/028335 | 4/2004 |
| WO | WO 2004/028336 | 4/2004 |
| WO | WO 2004/035106 | 4/2004 |

OTHER PUBLICATIONS

U.S. Appl. No. 10/166,025, filed Jun. 11, 2002, Lewkowicz et al.
U.S. Appl. No. 10/200,548, filed Jul. 23, 2002, Glukhovsky et al.
U.S. Appl. No. 10/213,345, filed Aug. 7, 2002, Glukhovsky.
U.S. Appl. No. 10/724,109, filed Dec. 1, 2003, Glukhovsky et al.
U.S. Appl. No. 60/279,406, filed Mar. 29, 2001, Avni et al.
U.S. Appl. No. 60/297,761, filed Jun. 14, 2001, Lewkowicz et al.
U.S. Appl. No. 60/301,141, filed Jun. 28, 2001, Glukhovsky et al.
U.S. Appl. No. 60/309,181, filed Aug. 2, 2001, Glukhovsky.
"Deep Subsurface Imaging in Tissues Using Spectral and Polarization Filtering". S G Demos Jul. 3, 2000 vol. 7, No. 1 Optics Express, pp. 23-28.
International Search Report for PCT/IL99/0554 dated Apr. 4, 2000.
International Search Report of PCT/IL02/00391, dated May 19, 2003.
International Search Report of International Application No. PCT/IL02/00526, Dated Mar. 7, 2003.
Katgraber F, Glenewinkel F, Fischler S, Int J. Legal Med 1998; 111(3) 154-6.
Supplementary Partial European Search Report, Mar. 19, 2004.
U.S. Appl. No. 60/414,339, filed Sep. 30, 2002, Iddan.
U.S. Appl. No. 60/458,441, filed Mar. 31, 2003, Gilad.

* cited by examiner

180
IN-VIVO SENSING SYSTEM

CROSS-REFERENCE TO RELATED APPLICATIONS

This application is a National Phase Application of PCT Application PCT/IL2003/000784, filed Sep. 30, 2003, which claims priority of U.S. Provisional Application 60/458,441 filed Mar. 31, 2003, and U.S. Provisional Application 60/414,339 filed Sep. 30, 2002 all of which are being incorporated by reference herein in their entirety.

FIELD OF THE INVENTION

The present invention relates to the field of in vivo sensing, for example imaging. Specifically, embodiments of the present invention relate to wide or moveable field in vivo imaging or other sensing.

BACKGROUND OF THE INVENTION

In vivo sensing can be used for non-invasive diagnostics. Imaging of body lumens typically involves the use of remote imaging devices. Typically, these imaging devices include illuminating capabilities. Certain remote imaging devices can be fitted with directional activators that allow an operator of the remote imaging device to direct the imaging head of the remote imaging device in a particular direction or towards a particular object. Other imaging devices do not accommodate directional activators due to constraints in size, availability of power or the necessity for rigid construction of the remote imaging device.

Swallowable imaging capsules or other suitable devices may be inserted into the gastrointestinal (GI) tract and moved passively through the small intestine by peristalsis while imaging the small intestine. However, passive movement of objects through larger body lumens, such as, the stomach or the large intestine may be slow and unpredictable. Furthermore, the device may be trapped in a fold of the walls of the body lumen. In such a position, an illuminating and imaging device may not have a sufficiently wide field of image and/or field of illumination to obtain images suitable for diagnostic purposes. In these cases monitoring and diagnosing larger body lumens may be not efficient.

Although, some in vivo sensors move through body lumens and can be remotely controlled, it is sometimes desirable to affix or otherwise restrict the movement of a sensing device in vivo for continuous sensing of an in vivo site, for example for post surgery monitoring. One drawback of affixing a sensor such as an imager to an in vivo site is that the direction of the imager and the orientation of the images captured may be limited by the orientation of the imager as it was affixed in vivo. A single, fixed orientation of an in vivo imager or other sensor may be insufficient to capture data or images of an entire area of interest of an in vivo lumen. Similarly, the size of an in vivo area of interest may be greater than can be imaged by an in vivo imager affixed at a designated orientation.

There is therefore a need for an in-vivo imaging device whose field of view may be changed so as to provide a wide or otherwise moveable field of view.

SUMMARY OF THE INVENTION

Embodiments of the present invention disclose an in vivo sensing system incorporating a sensing device which may be moved, for example, in a friction-reduced manner. In one embodiment of the invention the sensing device is movably disposed within a typically transparent housing or outer covering such that the orientation of the sensing device may be easily changed in response to substantially small forces, for example, gravitational forces, or electromagnetic torque generating fields, magnetic torque generating fields, or in response to other suitable mechanical or other stimuli. According to one embodiment the sensing system includes a friction reducing mechanism for reducing friction between the sensing device's outer surface and the in vivo housing's internal surface. For example, in one embodiment the sensing device is an imaging device is suspended within a liquid encapsulated within a housing or outer covering or shell. A small external actuation exerted on the imaging device, for example, may thereby be sufficient to alter the orientation of the imaging device thereby changing its line of sight or to permit the rotation of the imaging device within the housing. The field of view that can be captured by the imaging device may be widened. In one embodiment the external actuation may orient the optical axis to any desired direction. Other friction reducing devices, such as bearings may be used.

BRIEF DESCRIPTION OF THE DRAWINGS

The present invention will be understood and appreciated more fully from the following detailed description taken in conjunction with the drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Figure 1A:
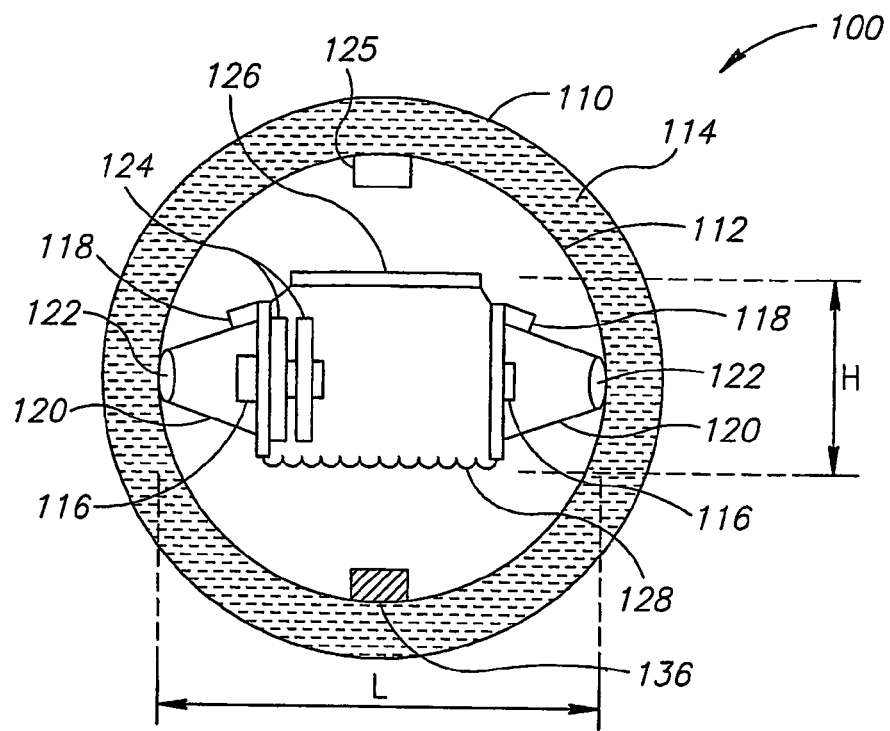
FIGS. 1A and 1B are simplified conceptual illustrations of an imaging system incorporating an imaging device suspended in a liquid and encapsulated by a housing constructed and operative in accordance with an embodiment of the present invention.

Reference is made to FIG. 1A which is a simplified conceptual illustration of a sensing system such as an imaging system 100 incorporating a sensing device such as an imaging device 112 suspended in a liquid 114 encapsulated within an outer covering housing 110 constructed and operative in accordance with an embodiment of the invention. The housing 110 may be, for example, spherical, ovoid, or any other suitable shape; the housing 110 may be partially deformable. The imaging device 112 may likewise be spherical, ovoid, cylindrical or any other shape movable within the housing 110. The imaging device 112 typically includes at least one imaging sensor 116. In FIG. 1A the imaging device 112 is spherical and includes two imaging sensors 116, each including, for example a lens 122 and a lens holder 120, which may be situated at diametrically opposed sides of the imaging device 112, as well as one or more (e.g., a pair) illumination sources 118 which illuminate the areas to be imaged by each of the imaging sensors 116. Other positions for image sensors may be used. More than one illumination source per imager may be used. The system 100 may be inserted into a body lumen for in vivo imaging. In one embodiment of the system 100 may include another sensor 125, e.g. blood detection sensor, pH sensor, electrical impedance sensor, pressure sensor, and temperature sensor, etc. According to one embodiment the system 100 is a swallowable device. In body lumens such as the stomach or large intestine one imager may be suitable for imaging objects at a distance of about 50-60 mm from the image sensor while another imager may be suitable for imaging objects at a distance of about 0-15 mm from the image sensor. The distance at which the imager images objects may be designated by defining parameters such as light intensity, exposure time or video signal gain. Other suitable parameters may be used as well. Increasing the light intensity, exposure time, or video signal gain may serve to image objects positioned at a further distance. Decreasing light intensity, exposure time, or video signal gain may serve to image objects at a closer distance. Other configurations of sensing device and imaging sensors may be used, such as for example, two imaging sensors 116 configured at, for example, right angles to each other, an imaging sensor 116 and a pH sensor, an imaging sensor and a blood detection sensor, temperature sensor etc. Other suitable outer coverings or housings may be used.

Preferably, each of the housing 110 and the liquid 114 are partially transparent or substantially transparent relative to the wavelength or wavelengths of the light used by the imaging sensor 116 or by the illumination source 118 to illuminate the area to be imaged. That the liquid 114 may have a diffraction coefficient that is similar to the diffraction coefficient of the housing 110 in order to minimize diffraction of the light reaching the imaging sensors 116. The liquid 114 may be of various suitable viscosities. According to one embodiment, the imaging device 112 has a specific gravity that is substantially equal to or smaller than the specific gravity of the liquid 114 so that the imaging device 112 is movably buoyant, and floats within the liquid 114. According to one embodiment, the weight of the imaging device 112 is evenly distributed along its length (L) and its height (H), or other suitable sets of axes, so that gravity does not favor a particular orientation of the imaging device 112 within the liquid 114. The weight may be evenly distributed along one or more axes, but not along others. Examples of suitable liquids 114 include, inter alia, water, saline solution, oil, glycerin, and bodily fluids. Other suitable liquids may be used.

An in vivo imaging system, according to one embodiment of the invention may be designed to image a patient's gastrointestinal (GI) tract. The imaging system may be ingested or otherwise inserted into the GI tract (such as by an endoscope) and may then be moved through the GI tract by, for example, the natural action of peristalsis. In another embodiment the imaging system may be positioned in other areas of the body (such as by a catheter, or by surgery, etc.), including the heart, blood vessels, lungs, urogenital system, etc. The imaging device 112 may include components and operate similarly to the imaging systems described in U.S. Pat. No. 5,604,531 to Iddan, et al., WO 01/65995 and/or WO 02/054932, each assigned to the common assignee of the present application and each hereby incorporated by reference. Furthermore, a reception, processing and review system may be used, such as in accordance with embodiments of U.S. Pat. No. 5,604,531 to Iddan, et al., WO 01/65995 and/or WO 02/054932, although other suitable reception, processing and review systems may be used. An imaging device that may transverse a patient's GI tract periodically imaging the GI tract may be, for example, an in vivo video camera system, typically comprising at least one illumination source 118, such as light emitting diodes (LEDs) for illuminating an in vivo site, one or more batteries 124, at least one image sensor 116, such as a charge coupled device (CCD) or a complementary metal oxide semiconductor (CMOS) image sensor, and an optical system, typically including lenses 122 and/or mirrors (not shown) for imaging an in vivo site on to the at least one image sensor. Optionally, the imaging device may include a transmitter 126, such as for example a wireless transmitter, and an antenna 128, for transmitting image data to an external receiving unit (not shown). The transmitter 126 for example may transmit image signals to the external receiving unit so that images may be reviewed for example on-line. Other suitable review methods may be used as well. In other embodiments, the imaging device 112 may include different components or other combination of components, and may have other weight ratios or buoyancies. In one embodiment of the invention one or more sensors including blood detection sensors, pH sensors, temperature sensors, electrical impedance sensors, etc, may be incorporated in the system.

Figure 1B:
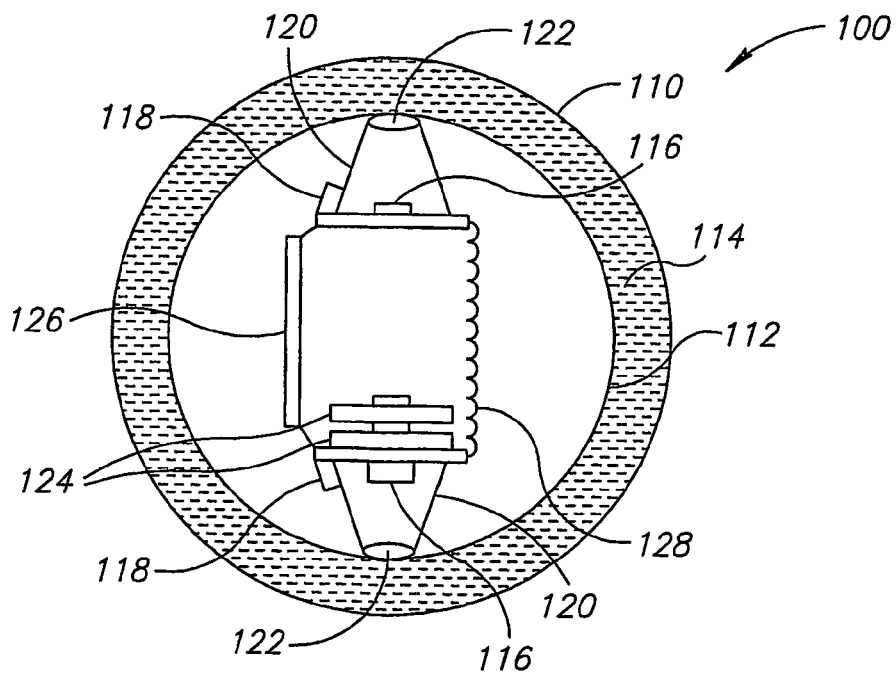

In an exemplary embodiment of the present invention, a slight external force or torque exerted on the imaging device 112 or the force of a small change in the directional flow of the liquid 114 may cause a change in the orientation of the imaging device 112 and thereby change its line of sight and/or cause the rotation of the imaging device within the housing and thereby widen the field of view. Such a change in the orientation of the imaging device 112 is depicted in FIG. 1B which shows a housing 110 and encapsulated liquid 114 in which is floating an imaging device 112 whose orientation has changed (for example, in relation to the embodiment illustrated in FIG. 1A). Preferably, the imaging device 112 is sufficiently buoyant within the liquid 114 that it can rotate freely within the housing 110. In such embodiment, the change in the orientation of the imaging device 112 may be caused by an external force on the imaging device 112 or a change in the directional flow of the liquid 114. Such change in the orientation of the imaging device 112 may permit the capturing of images from various vantage points and directions (as further illustrated, for example, in FIG. 5) and the widening of the field of view of the imaging device within a body lumen, e.g., the GI tract. On-line viewing of, for example, the transmitted images to the external receiving unit may provide feedback for positioning the imaging device to a desired orientation. Other suitable methods may be used as well for properly orienting the imaging device.

In further embodiments, the imaging device 112 may be weighted or arranged so that it holds substantially one orientation during, for example, its traverse of the GI tract, or tends to return to such orientation when moved from that orientation. For example, the imaging device 112 may be weighted so that, when suspended within the housing 110, it attempts to keep a certain orientation. In one embodiment one or more ballast weights 136 may be incorporated in the imaging device 112 for the purpose of keeping the imaging device at a specific orientation. The ballast weight may be in the form of a block, ring, or any other suitable shape. In other embodiments, specific weighting devices need not be used, and the device as a whole may include a weight distribution allowing for a specific orientation to be kept. In one embodiment of the invention, the imaging device 112 may tend to assume a position that faces, for example, down, up, to the side, or at some angle with respect to the direction of gravity. The line of sight of the imaging device may be altered for example by changing the orientation of the patient's body of which the device is incorporated so as to change the line of gravity with respect to the imaging device. For example, the patient may be asked to lay down on his back or stomach, or alternatively recline at specified or different angles. In one embodiment of the invention, the ballast weight may be positioned so that at least one imaging device always faces up in the opposite direction of gravity. Other suitable orientations may be used.

The housing 110 may be configured for insertion in vivo, for example, for being swallowed or otherwise placed in the GI tract, or for being inserted into other body lumens such as the urogenital system, the lungs, heart, blood vessels, etc. The housing 110 may be manufactured from any material suitable for being inserted in vivo, such as, for example, plastic or glass. Typically, the housing 110 is substantially transparent relative to the wavelength or wavelengths used for imaging or of the illumination.

The liquid 114 may be present in the housing 110 at the time that the housing 110 is inserted in vivo. Alternatively, and in certain embodiments of the present invention, the housing 110 may be formed from a collapsible material, which may expand and assume a pre-designated shape when exposed to certain moisture, acidity or other environmental conditions. In one embodiment of the invention, for example, a material forming the housing 110 may, at the time that it is introduced in vivo, be collapsed into a small size and volume and encapsulated in a hydrocarbon casing such as, for example, a gelatin capsule or other structure. The hydrocarbon casing may dissolve in the acidic environment, for example of the stomach, thereby freeing the material, which forms the housing 110 to assume a larger volume and pre-designated shape. In this way, the dimensions of the housing 110 may be small when swallowed and then may expand and assume a spherical or other shape when exposed to a designated environmental condition in the GI tract. Such material forming the housing is preferably, in one embodiment comprised of selectively porous substances to permit liquid 114 in the GI tract, such as water, saline or any other liquid present or introduced to the GI tract, to percolate or diffuse into the housing 110 during or after the expansion of the housing 110 into its larger volume or pre-designated shape. Examples of such selectively porous materials could include known permeable or semi-permeable membranes. For example, a suitable plastic can be used. For example, water introduced into the GI tract may percolate through the selectively porous material of the housing 110. The selectively porous material may then expand, or unfold and increase the volume of the housing 110 to a larger size or pre-designated shape. According to other embodiments the housing may be made of a suitable rubber. Other suitable materials may be used.

Figure 2:
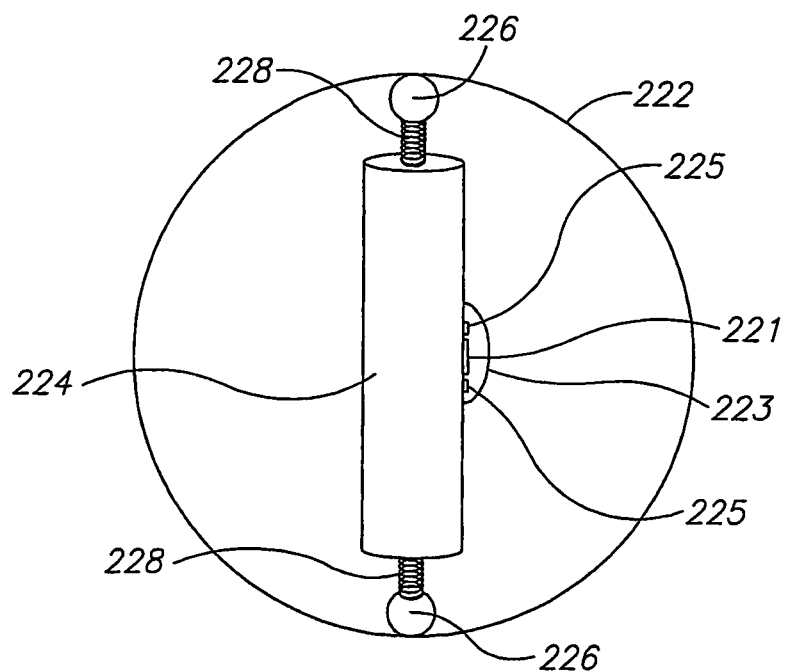
FIG. 2 is a schematic illustration of an imaging system according to another embodiment of the present invention.

In another embodiment of the present invention depicted in FIG. 2 there are included a housing or other suitable outer covering or encapsulation 222 encasing an imaging device 224 fitted with a mechanism including at least two friction reducing elements or bearings, such as, ball bearings 226 or other bearings. The housing 222 may either include or not include an encapsulated liquid. The shape of the housing 222 may be, for example, spherical, ovoid, or any other suitable shape; the housing may be partially deformable. The imaging device 224 may include at least one image sensor 221 and at least one illumination source 225. The various components may be positioned behind an optical window 223 and may further comprise elements as described above. According to one embodiment the image sensor 221 is at an essentially non-parallel orientation in relation to the longitudinal axis of the device 224. The imaging device 224 may rest on or be attached to a mechanism including at least two friction-reducing ball bearings 226 so that the imaging device 224 moves relatively freely within the housing. The friction-reducing ball bearings 226 may be attached to the imaging device 224 by way of, for example, a spring 228 that may keep the friction reducing ball bearing 226 in contact with the internal surface of the transparent housing 222. Other suitable methods of mounting an imaging device using ball bearings or other bearings may be used; for example methods not using springs. Contact between the friction-reducing ball bearings 226 and the internal surface of the housing 222 preferably limits direct contact between the imaging device 224 and the internal surface of the housing 222 such that the imaging device 224 can move freely and possibly rotate within the housing. The image sensor 221 of the imaging device 224 may be situated away from the friction-reducing ball bearing 226 so that its view is not impaired by the placement of the friction-reducing roller bearing 226. In alternate embodiments of the present invention, the housing 222 and the image device 224 may have other shapes.

Figure 3A:
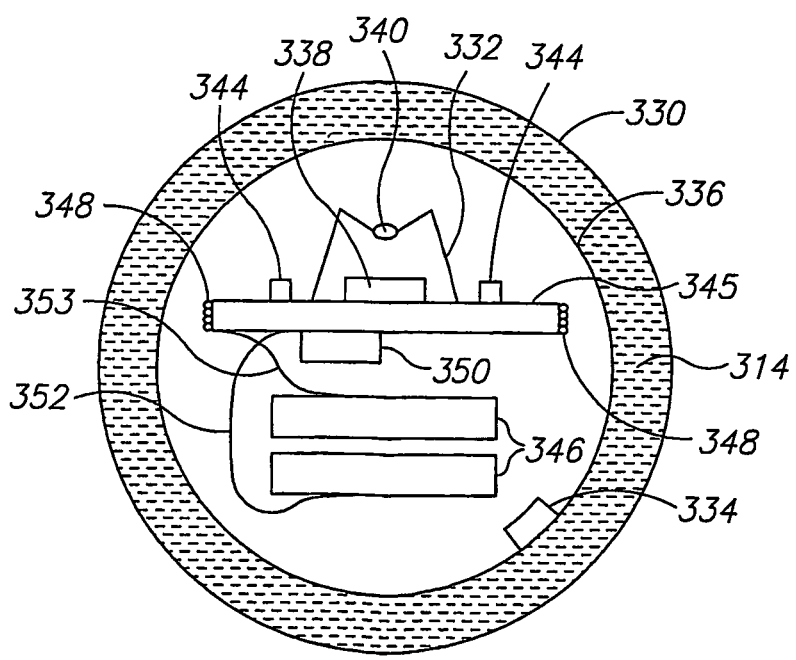
FIGS. 3A and 3B are schematic illustrations of an imaging system incorporating a moveable imaging device according to other embodiments of the present invention.
Figure 3B:
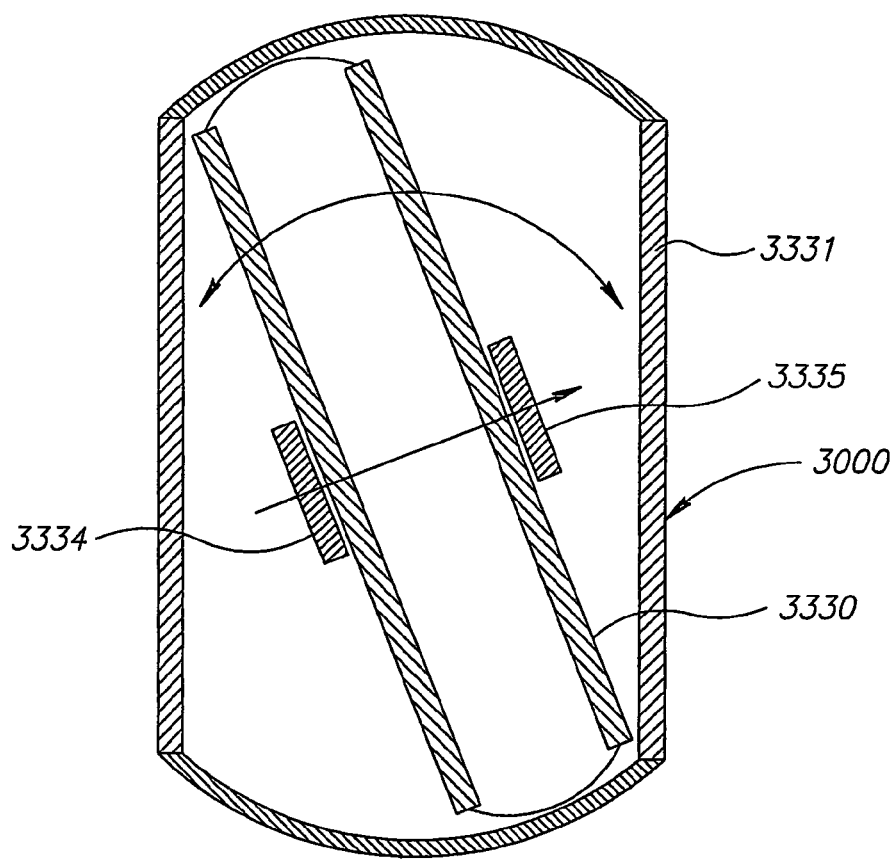

Imaging systems according to other embodiments of the invention are illustrated in FIGS. 3A and 3B. Imaging device 336 in FIG. 3A is disposed within a housing 330 and typically liquid 314 is disposed in between the housing and imaging device, such as described herein. The imaging device 336 may includes a directional activator such as a magnet 334. The device may include an imaging device such as an optical transducer (e.g., a CMOS 338, a charge couple device (CCD) or other suitable devices), a lens or lens system 340 mounted on a lens holder 332 which may fix the lens 340 in a fixed position relative to the CMOS 338. An illumination portion of the optical head assembly may have one or more light emitting diodes (LED) 344. In alternate embodiments, other illumination sources may be used. In yet further embodiments, the illuminating and/or the imaging portion may be integrated with or in close vicinity to the surface of the imaging device 336. The device may contain other elements, such as batteries 346 which may be, for example electrically connected to circuit board 345 with springs 352 and 353, and controller or processor 350. For example, the processor 350 may include an application specific integrated circuit (ASIC) having transmitting capabilities, for example, operating on a minimum shift keying (MSK) modulation system to effect transmitting of digital signals through one or more antennas 348 on radio frequencies to a receiving system (not shown). One or more antennas 348 may be coiled around circuit board 345, for example, as is shown in FIG. 3A or may be embedded on a circuit board 397 (e.g., as in FIG. 4). Other suitable positioning of an antenna may be applied as well. The processor may also control the illumination and imager, for example as described in the above mentioned WO 01/65995. In alternate embodiments, other signals and other electronic and processing components may be used. Other components and configurations of components are possible.

According to an embodiment of the invention an external magnetic field or force (not shown), which may be time-varied, may be created in the vicinity of a body in which a system, such as the system described in FIG. 3A, is disposed. The magnetic field or force may typically be used to rotate or otherwise maneuver the magnet 334. The magnetic field may be created, for example, by a stationary or mobile portable power source, which is placed in proximity to the patient's body, typically generating an electromagnetic field that substantially surrounds the patient's body. The strength and the direction of the generated magnetic field may be altered to move the imaging device in different directions. In other embodiments, the field need only surround the relevant portion of the patient, for example the abdomen. In another embodiment the magnetic field may be created with electrodes or coils placed on the housing 330 encapsulating the system. The magnetic field may be externally controlled or preset.

A magnetic field can be generated continuously or when necessary. The power source may include an AC induction coil, e.g., a low frequency AC induction coil (about 60 Hz or other suitable rates) or may have a rotating magnetic circuit to generate a varying magnetic field. In order to achieve higher efficiency of the energy transmission it may be desirable to operate in a relatively high frequency range. However, due to high attenuation of the body tissues at high frequencies—the practical frequency range may be from several tens of Hz to several tens of KHz. The magnet 334 typically moves in accordance with the direction of the applied magnetic field. The movement of the magnet 334 may cause the whole imaging device 336 to move within the housing 330. Thus, according to an embodiment of the invention, an imaging device may be controlled to move, typically around its axis, so as to obtain a larger view of imaging. On line viewing of the transmitted images may provide proper feedback on the orientation and field of view of the imaging device. Other suitable means of tracking the line of sight of the imaging device may be used.

Similarly, the system 3000 that is illustrated in FIG. 3B, includes an oblong device within an oblong container, such as a capsule or an almost capsule shaped, or oblong and/or ovoid shaped, imaging device 3330 disposed within an almost capsule shaped, or oblong and/or ovoid shaped, housing 3331. The imaging device 3330 may have at least two magnets 3334 and 3335, each magnet positioned differently, such as at a different side of the imaging device 3330. By applying a magnetic field from different sides of or directions relative to the system 3000 (or a patient with a system 3000) the imaging device 3330 may be made to move to certain (e.g., two) sides, essentially moving about its axis to enable a wide view to an imager (not shown) within the imaging device 3330.

Figure 4:
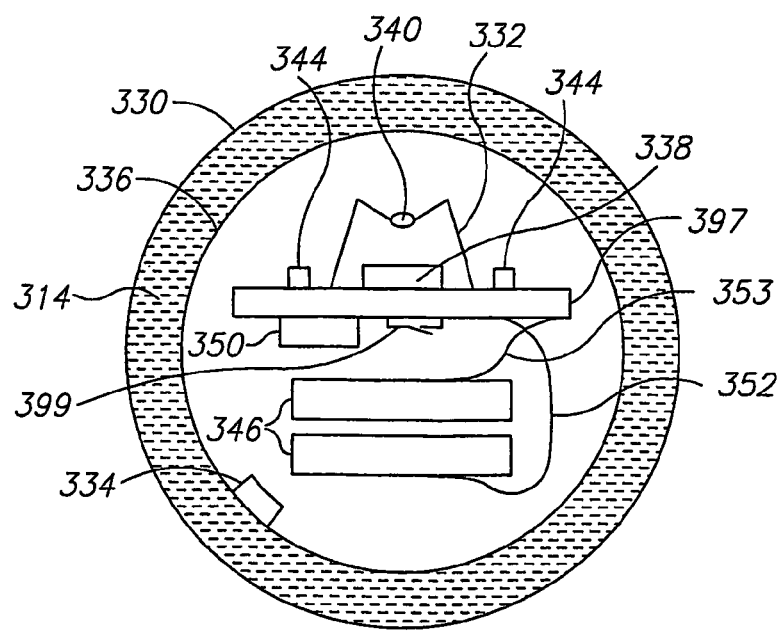
FIG. 4 is a schematic illustration of an in vivo imaging system incorporating an imaging device moveably suspended within a housing capable of altering an operational mode in response to a magnetic field, in accordance with an embodiment of the invention.

Reference is now made to FIG. 4, which is a simplified illustration of a system including an imaging device suspended within a housing or encapsulation capable of altering an operational mode in response to a magnetic field, in accordance with an embodiment of the present invention. In certain embodiments, a magnetic switch 399 may be configured to control at least one electrical component of imaging device. The magnetic switch 399 may be configured between portions of the electrical circuitry of imaging device 336, such that when magnetic switch 399 is open, some or all components of imaging device 336 are powered off or on. Magnetic switch 399 may be constructed of a magnet or materials responsive to magnetic forces such that it may be moved upon exposure of imaging device 336 to a magnetic field. Alternately, other suitable control circuits may be used.

In certain embodiments, magnetic switch 399 may, for example, be situated so as to provide a connection between one or more batteries 346 or other suitable power sources and circuit board 397 of imaging device 336, such that when magnetic switch 399 is in an off position, the power supply to imaging device 336 is off, and when magnetic switch 399 is in an on position, imaging device 336 is powered on. In other embodiments, magnetic switch 399 may connect other components of imaging device 336 to turn imaging device 336 on or off, to activate or deactivate other functions of imaging device 336, or to otherwise change an operation mode of imaging device 336.

In certain embodiments, magnetic switch 399 may be configured to retain a position to which it is moved even after a magnetic field has been removed. In other embodiments, magnetic switch 399 may be, for example, hinged with a spring such that magnetic switch 399 resumes its prior position after a magnetic field has been removed. In a resting state, magnetic switch 399 can be set in an off position such that when imaging device 336 is exposed to a magnetic field, magnetic switch 399 moves into an on position, and activates imaging device 336. Alternatively, magnetic switch 399 can be set to an on position and turned off upon exposure to a magnetic field. Other settings are possible, and other suitable switch configurations are possible.

In certain embodiments one or more magnetic switches 399 with varying resistances to magnetic forces may be included in an imaging device 336 to, for example, control settings of an imaging device 336 in accordance with the strength or other characteristics of the magnetic field to which imaging device 336 is exposed. For example, a series of magnetic switches 399, secured by, for example, hinges with a different resistances may connect components of the imaging device 336. Alternatively, a single magnetic switch 399 with various settings, each with a particular resistance, may be used. For example, when imaging device 336 is exposed to a weak magnetic field, a magnetic switch 399 may change positions initiating a particular action by imaging device 336, such as for example, capturing images at a rate of, for example, one frame per second. When imaging device 336 is exposed to a stronger magnetic field, a different magnetic switch with a stronger resistance may be activated initiating another action, such as for example, capturing images at a rate of, for example, two frames per second. Other suitable mode changes and other suitable frame rates may be used. Alternatively, the same magnetic switch 399 may be moved into successive settings with increases in the strength of a magnetic field to which it is exposed.

Figure 5:
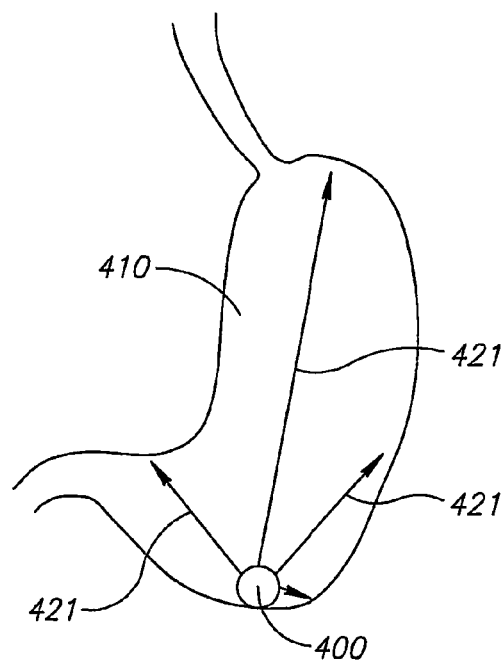
FIG. 5 is a schematic illustration of an in vivo field of view afforded by an imaging system according to an embodiment of the invention.

As schematically illustrated in FIG. 5, a system 400 including an imaging device, according to embodiments of the invention, which may be situated in a patient's stomach 410, may be moved so as to enable the imaging device (not shown) a wide-angle view (as demonstrated by the arrows 421). With other configurations and in other environments, other ranges of view are possible.

Figure 6:
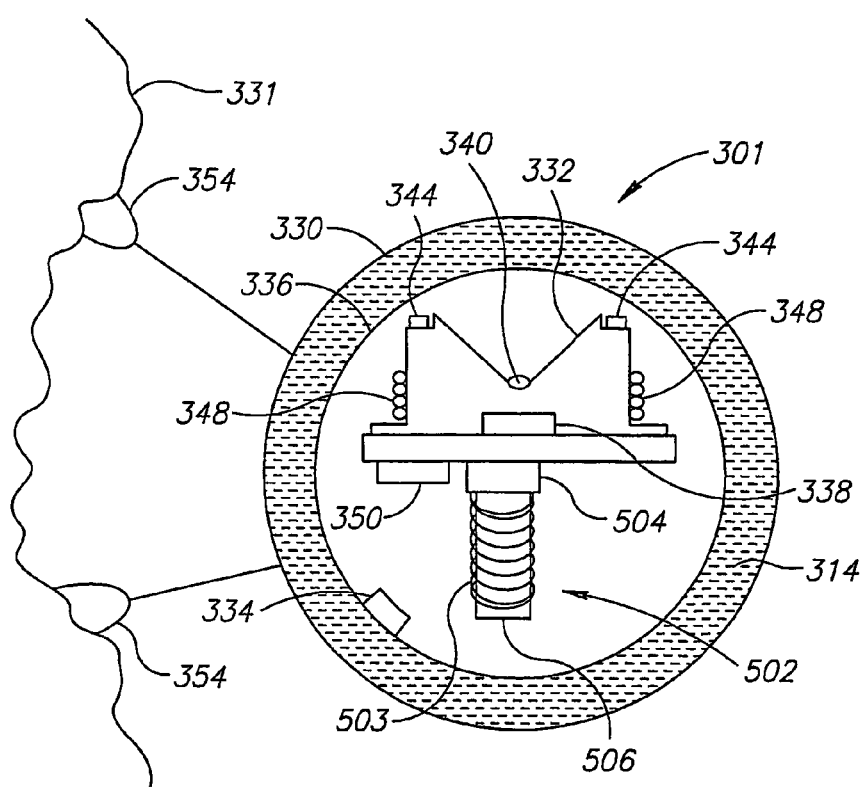
FIG. 6 is a schematic illustration of an in vivo imaging system incorporating an imaging device moveably suspended within an anchorable housing capable of receiving power from an external energy source, in accordance with an embodiment of the present invention.

Reference is made to FIG. 6, which is a simplified illustration of a sensing device such as an imaging device 336 suspended within an anchorable housing 330 capable of receiving power from an external energy source, in accordance with an embodiment of the present invention. Energy receiving unit 502 may include an element 503, for example a conductive coil, configured for receiving energy from an external energy source, a rectifier circuit 504 for converting AC voltage to DC voltage and a capacitor 506. A capacitor 506 ranging from several mili-Farads to a few hundred mili-Farads may be used (other suitable ranges may be used) or alternatively, a chargeable battery (not shown) may be used for storage of the voltage required for operation of the electrical components of the housing 336. For example, a capacitor of about 10 Farad and 5 m Watt may be suitable for use in one embodiment of the present invention.

In one embodiment of the invention, imaging system 301 may be inserted into an in vivo area, such as for example in the vicinity of the surgical site 331. A surgeon may affix housing 330 by way of, for example, clasps 354. Constituents such as fasteners, glue, thread or fiber attached to housing 330 with one or more rings or indentations, or any other suitable attachments may be used. In certain embodiments, imaging device 336 may remain in vivo and capture and transmit images or other data of the surgical site 331. Energy-receiving unit 502 may receive a charge from an external energy source (not shown), for example a transcutaneous charge, on a continuous, periodic or occasional basis to provide power to the imaging device 336. In certain embodiments, a three axial coil may be used to ensure that energy may be produced from a unidirectional magnetic field regardless of the directionality of the energy-receiving unit 502. In certain embodiments it may be possible to provide power to the imaging device 336 on a continuous, occasional or periodic basis such that imaging device 336 captures images on a continuous, periodic or occasional period of days, weeks or longer. In other embodiments, imaging device 336 may be powered-on by way of, for example, a transcutaneous charge from an external energy source, at such times as a user or medical practitioner desires to capture images of the in vivo site.

The function and operation of energy receiving unit 502 may be, for example similar to those described in certain embodiments of U.S. patent application Ser. No. 10/115,585, published as U.S. 2002/0165592 A1, which is assigned to the common assignee of the present invention and which is hereby incorporated by reference; however, other suitable energy transmission and reception systems and methods may be used.

Figure 7A:
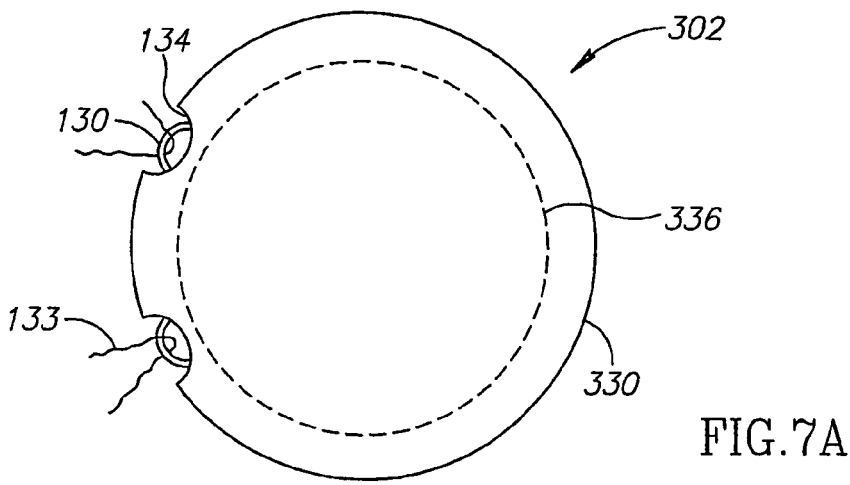
FIGS. 7A, 7B, and 7C are schematic illustrations of anchorable housings incorporating a moveably suspended imaging device according to embodiments of the present invention.

FIG. 7A schematically illustrates a front view of an imaging system 302 according to an embodiment of the invention with an attachment mechanism including, for example, one or more (in the example shown two) rings 130 on its perimeter. Rings 130 may be fit into depressions in the housing body 134 perimeter so that they do not protrude from the housing 330 perimeter and do not obstruct the housing's passage through the GI tract; however, the rings 130 may be in other configurations. Rings 130 may be used for sewing or otherwise attaching the housing 330 to, or otherwise restricting the movement to, a desired location in vivo, for example in the vicinity of a surgical site in the GI tract. Devices according to embodiments of the present invention may be used in other body lumens. Following a surgical operation, for an example, in the GI tract, a surgeon may place imaging system 302 at a location in the vicinity of the surgical site. The surgeon may affix housing 330 in place by sewing a suture through rings 130 and through the tissue at the site, such as for example, the walls of a body lumen. The housing 330 may thus be fastened to the tissue. It should be appreciated that one or more rings 130 can be used in the invention, depending, inter alia, on the shape of the housing 330 and the contours of the in vivo site.

Imaging system 302 may remain affixed to the in vivo site, and may capture images thereof from varying orientations as are assumed through the movements of imaging device 336 within housing 330, according to embodiments of the invention. In some embodiments, images captured by imaging device 336 may be transmitted to an external receiving, processing, viewing and/or monitoring station (not shown) that may receive and display such images. In alternate embodiments, data other than image data may be collected.

Figure 7B:
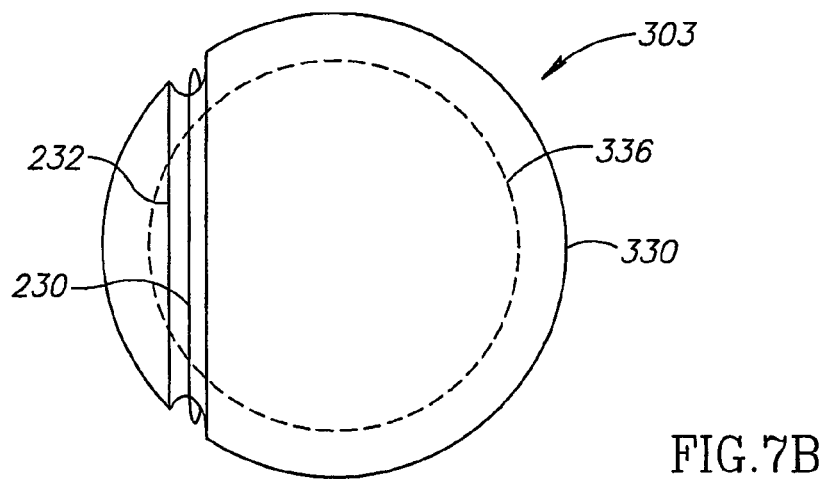

FIG. 7B schematically illustrates a front view of an imaging system 303, having an attachment mechanism including, for example, an indentation 232 that may circle or surround, either in part or in whole, the housing's 330 perimeter. Such indentation may be more or less around the center of the housing 330 body or may be situated elsewhere on the housing 330. Indentation 232 may form a groove suitable for accommodating a fiber or thread 230 such as for example an operating doctor's thread. The housing 330 may thus be fastened to the surgical site by thread 230 which surrounds or otherwise holds the housing 330 and which is anchored onto the patient's body. Other shapes of grooves or indentations may be used and other areas on the housing 330 may be used for affixing thread 230 to a body. Typically, thread 230 used for suturing the housing 330 to a surgical site in vivo is thread, which may disintegrate with time. Other types of thread may be used. Thus, a doctor performing an operation in the gastrointestinal tract may activate the system 303 (e.g., initiate imaging or other sensing) in housing 330 and sew in or otherwise attach housing 330 at the operation site, such as for example, in the gastrointestinal tract prior to closing the surgical incision. Other in vivo sites may be sensed, and sensing may include sensing other than imaging, such as sensing pH, temperature, pressure, electrical impedance, etc. The sensing (such as imaging), which may be continuous or periodic, may last through a critical post surgical period. In certain embodiments such as for example those described above, imaging device 336 may be turned on or off to image the in vivo site at varying or designated times. During this time or when the imaging device 336 is on, the surgical site may be imaged or other data may be collected, and the images or data may be transmitted to a receiving system, such as an external workstation (not shown), where the images or data may be monitored by an external operator.

Figure 7C:
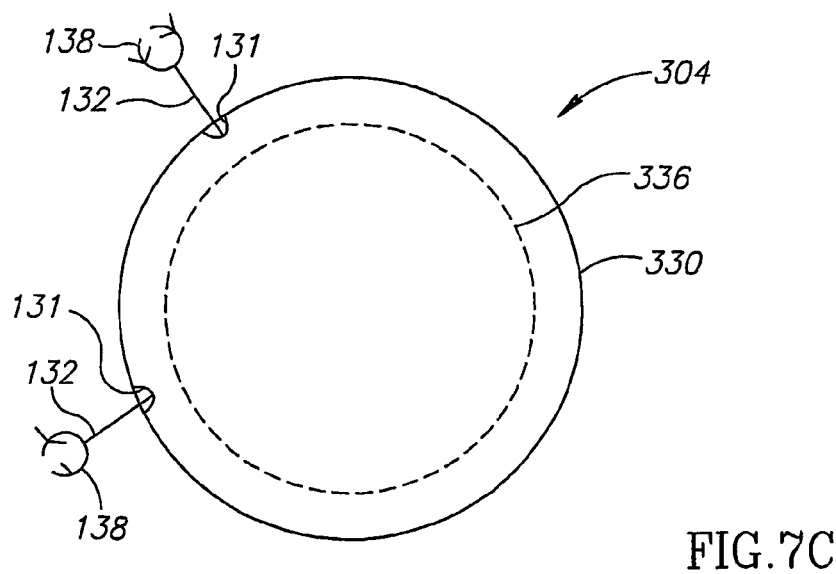

FIG. 7C illustrates an imaging system 304 which includes an attachment mechanism including, for example, a niche 131 to receive an anchor 132 into housing 330. Anchor 132 may include, for example, fasteners 138. Anchor 132 typically extends from the housing 330, and fasteners 138, may grasp an internal body tissue. Fasteners 138 may hold on to a section of internal body tissue by, for example, slightly piercing or pinching the tissue, through suction or by other suitable methods or systems. Other suitable number and type of fasteners 138 such as for example, pins, screws, suction cups, or clasps may be used. In certain embodiments, fasteners 138 may be directly attached to housing 330. Fasteners 138 may in certain embodiments be made of materials that disintegrate over time in a body, such that housing 330 may be released into, for example the gastrointestinal tract, where it may be driven by peristalsis and naturally excreted from the body. Such a release may obviate the need to manually remove the housing from a patient.

At some point in time, for example, during the imaging process or after its termination, the sutures sewn through rings 130 or around housing 330 in indentation 232, or fasteners 138 which have been immobilizing or otherwise attaching the imaging system 304 to the surgical site, may disintegrate, and imaging system 304 may be released into the gastrointestinal tract. Imaging system 304 may be free to travel through the GI tract, for example, driven by peristalsis and may naturally be excreted from the body. Embodiments of the system and method of the invention may thus enable post surgical monitoring or data collection in the gastrointestinal tract or another in vivo sites without having to leave an opening in the patient's body or without having to operate on the patient a second time in order to retrieve the monitoring system. In other embodiments an imaging system comprising an imaging device 336, as described above, may be designed for surgical sites other than the GI tract, such as the lungs, heart, blood vessels, reproductive tract or urogenital system. In certain embodiments a housing 330, may include, for example, one or more fasteners 138 for immobilizing the housing 330 to a site of interest at the time of surgery and for being later removed, for example, through an incision or through a transthoracic, transesophageal opening, or any other suitable opening.

Figure 8:
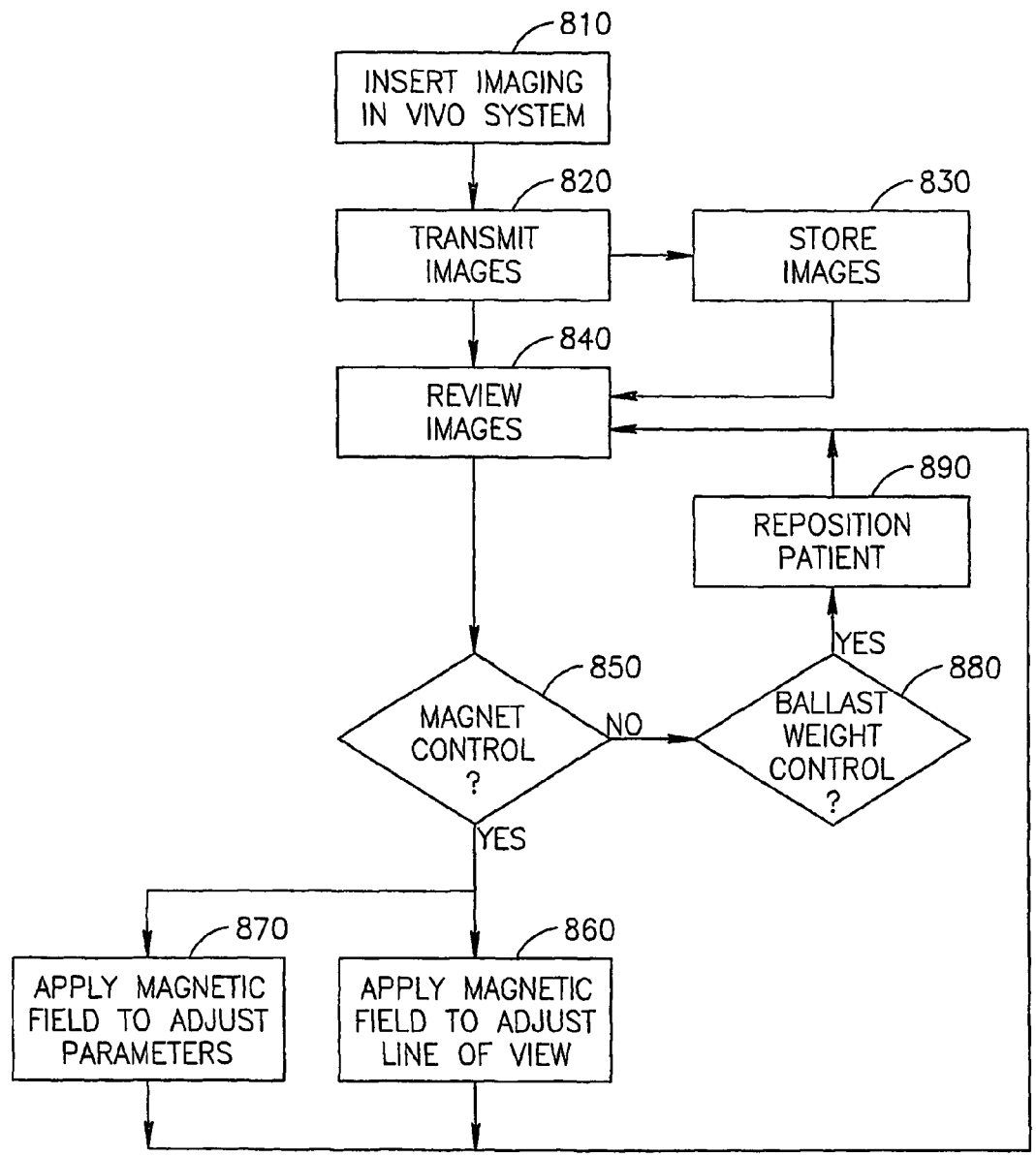
FIG. 8 is a flow chart exemplifying a method for imaging an in vivo site according to one embodiment of the invention.

According to one embodiment of the invention, there is provided a method for imaging an in vivo site. According to one embodiment the method includes the step of enabling an in vivo sensing device to be moved in a friction-reduced manner. In other embodiments, providing a system allowing friction reduced movement need not be used. According to one embodiment the in vivo sensing device is disposed within a housing. An external force may be applied to initiate a movement of the sensing device. FIG. 8 shows a flow chart describing a method for imaging an in vivo site according to one embodiment of the invention. In block 810 an imaging system which may include a structure enabling a sensing device disposed within a housing to be moved in a friction-reduced manner is ingested. Other methods of introducing an imaging system may be used as well for example by positioning the imaging system with a catheter, needle and/or endoscope. An imaging system such as in embodiments shown herein may be used; other embodiments of the method may use other suitable systems. Images from the in vivo imaging system may be transmitted externally (820), for example to a suitable receiving system, and a health professional may review the transmitted images (840). According to some embodiments images may be stored (830), for example, in an external recording device; such storage may be, for example, before or concurrent with viewing. Based on the images reviewed or any other suitable parameter, the health professional may adjust the line of sight of the imaging device incorporated in the system. In block 850, if a magnetic control ability is included within the device, the method may proceed to one or both blocks 860 and 870, and if not, the method may proceed to block 880; other sequences are of course possible, not including blocks such as 860, 870 and 880. In other embodiments, magnetic control may be used for other control functions, and other methods of control may be used. In one embodiment of the invention a magnet may be included in the imaging system as described above and a magnetic field may be applied (860) to, for example, adjust the line of view. In a further embodiment, other parameters of the imaging system may also be adjusted by, for example, applying an appropriate magnetic field (870), for example, as is described in FIG. 4. In another embodiment of the invention, a ballast weight may be included in the imaging device. In block 880, if ballast weight control capability is included, the method proceeds to block 890; if not, other control may be used. In some embodiments, no active control may be used. If a ballast weight is used, in one embodiment, the ballast weight may lean toward the line of gravity. As such, the line of sight of the imager may be adjusted by, for example, repositioning the patient (890). A patient who has been repositioned from, for example, standing erect to lying flat on his back my change the line of sight of the imager by, for example, 90 degrees. Other steps or series of steps may be used. The friction reducing mechanism included in the imaging system and described above may allow the imaging device to alter its line of sight with minimal lag and with a small externally applied forces.

While the present invention has been described with reference to one or more specific embodiments, the description is intended to be illustrative as a whole and is not to be construed as limiting the invention to the embodiments shown. It is appreciated that various modifications may occur to those skilled in the art that, while not specifically shown herein, are nevertheless within the true spirit and scope of the invention.

The invention claimed is:

1. A method for imaging an in vivo site comprising the steps of:
    inserting within a body lumen an in-vivo imaging device comprising a magnet, said in-vivo imaging device being disposed within a housing without being mounted thereto so as to be freely movable within the housing in any rotational direction, and said in-vivo imaging device being surrounded by a friction reducing material within said housing;
    changing orientation of said in vivo imaging device to any direction with respect to said housing in a friction-reduced manner by application of an external force to said in-vivo imaging device; and
    capturing images from any of said orientations.

2. The method according to claim 1 wherein the external force is selected from the group consisting of: electromagnetic force torque generating fields, magnetic torque generating fields, and gravitational force.

3. The method according to claim 2 wherein applying an external force includes repositioning a patient.

4. The method according to claim 1 further comprising the step of:
    transmitting data from the in vivo imaging device.

5. The method according to claim 1 comprising the steps of:
    reviewing transmitted data; and applying an external force to change the direction of the imaging device based on the reviewed transmitted data.

* * * * *